United States Patent [19]

Uno et al.

[11] Patent Number: 4,529,540
[45] Date of Patent: Jul. 16, 1985

[54] HUMIDITY-SENSITIVE RESISTIVE ELEMENT

[75] Inventors: Shigeki Uno, Inagi; Mituo Harata, Kawasaki; Kazuo Sakuma, Tokyo; Hideaki Hiraki, Kawasaki, all of Japan

[73] Assignee: Tokyo Shibaura Denki Kabushiki Kaisha, Japan

[21] Appl. No.: 582,553

[22] Filed: Feb. 22, 1984

[30] Foreign Application Priority Data

Feb. 24, 1983 [JP] Japan .................................. 58-29723

[51] Int. Cl.³ .............................................. H01B 1/06
[52] U.S. Cl. .................... 252/518; 252/521; 338/35
[58] Field of Search .................. 252/518, 521; 338/34, 338/35, 308, 309

[56] References Cited

U.S. PATENT DOCUMENTS 3,926,858 12/1975 Ichinose et al. ...................... 252/518
4,045,764 8/1977 Ichinose et al. ...................... 252/518
4,052,691 10/1977 Nagano et al. ....................... 252/518
4,276,537 6/1981 Shimizu ............................... 252/518
4,347,495 8/1982 Hunter .................................. 338/34
4,447,352 5/1984 Inoue et al. ...................... 252/518 X
4,464,647 8/1984 Yokomizo et al. .................. 252/518

FOREIGN PATENT DOCUMENTS 0013022 7/1980 European Pat. Off. .
0033521 12/1981 European Pat. Off. .
1422182 1/1976 United Kingdom .

Primary Examiner—Josephine L. Barr
Attorney, Agent, or Firm—Banner, Birch, McKie & Beckett

[57] ABSTRACT

A humidity-sensitive element comprises a humidity-sensitive body which includes 21–73 mol % of $Cr_2O_3$, 25–55 mol % of at least one member selected from the group consisting of ZnO and MgO, 0.5–8.0 mol % of CuO, 0.5–8.0 mol % of $Li_2O$, and 0.5–8.0 mol % of $V_2O_5$, and a pair of electrodes attached to the body. Such an element provides excellent stability over a wide range of humidity and temperature levels.

8 Claims, 5 Drawing Figures

HUMIDITY-SENSITIVE RESISTIVE ELEMENT

BACKGROUND OF THE INVENTION

This invention generally relates to the field of humidity measuring devices and, more particularly, is directed to a humidity-sensitive resistance element for use in measuring humidity.

There are many devices known in the prior art for measuring the amount of humidity in the atmosphere. Many of these devices employ a humidity-sensitive element which varies in resistance depending on the amount of humidity exposed to the element. Thus, the element may be connected in an electrical circuit to provide an output signal representative of the amount of humidity present in the environment.

Most of the humidity measuring devices which employ a humidity-sensitive resistive element measure the amount of humidity by detecting a change in resistance value of the element. The resistance value of the element changes as a result of moisture physically adhering to the surface of the body of the element. The element body is usually made of a polymer, a sintered metal oxide or is formed from a metal oxide layer sintered on a substrate. Under low humidity conditions, the resistance value of such an element is very large, e.g., in the range 1 to 10 M$\Omega$. Thus, elements of this type cannot be used in electrical circuits without the addition of impedance matching means. Moreover, the degree of accuracy of such an element decreases with prolonged use. The decrease in accuracy is due to the surface of the element becoming contaminated over time, thus not allowing moisture to adhere to the body of the element.

A humidity-sensitive resistive element having a body made of metal oxide is disclosed in U.S. Pat. No. 4,080,564 issued to Nitta et al. Nitta discloses that the long-term accuracy of such an element can be improved by applying heat to the element before each use. The heat is used to clear away any contaminates which may be present on the surface of the element. The requirement that the element be heated before each use means that continuous monitoring of humidity is impossible. Furthermore, the addition of a heater and heating circuitry adds to the cost of the humidity measuring equipment.

Japanese Patent Disclosure No. 56-4204, published Jan. 17, 1981, discloses another humidity-sensitive resistive element. The element comprises 85 to 99 mol% of ZnO, 0.5 to 10 mol% of LiZnVO$_4$, and 0.5 to 5 mol% of Cr$_2$O$_3$+Fe$_2$O$_3$. The element has somewhat stable characteristics when it is used over a long period of time at relatively low temperatures and in normal environmental conditions (as for example, 0° to 40° C. at 30 to 90% relative humidity). The element may thus be used in air conditioners and humidifiers. The element, however, may not be used in high temperature environments as the accuracy of the element is adversely affected.

Another type of humidity-sensitive resistive element is described in U.S. Pat. No. 3,926,858 issued to Ichinose et al., and comprises 89.9 to 20 mol% of ZnO, 0.1 to 20 mol% of Cr$_2$O$_3$ and 10 to 60 mol% of at least one member selected from the group consisting of a third metal oxide. It is disclosed that when the content of Cr$_2$O$_3$ is more than 20 mol%, the resultant element has a resistivity of over 100 M$\Omega$ and is, therefore, unsuitable as a moisture-sensitive element. While the resistance range of the humidity-sensitive element disclosed by Ichinose is lower than some elements known in the art, it it still very high and must be used with an impedance matching network.

The instant invention overcomes the above disadvantages of humidity-sensitive resistive elements known in the prior art by a novel selection of the semiconductor materials which forms the element. In particular, the present invention produces a humidity-sensitive element having a relatively low electrical resistance range and which exhibits good stability, even after prolonged use at high temperatures. The element does not have to be heated before each use in order to maintain its accuracy. Thus, continuous monitoring of humidity is possible. The element also does not require an impedance matching network and may be directly connected into an electrical circuit. The element may also be used over a wide range of humidity conditions and over a wide range of temperatures.

SUMMARY OF THE INVENTION

It is an object of the present invention to provide a humidity-sensitive element having highly stable and accurate humidity sensing characteristics.

It is a further object of the present invention to provide a humidity-sensitive element having a relatively low electrical resistance range which is suitable for directly connecting the element to a humidity measuring circuit.

It is another object of the present invention to provide a humidity-sensitive element having an electrical resistance range which is suitable for use over a wide range of humidity measurements.

It is a still further object of the present invention to provide a humidity-sensitive element having a high sensitivity for measuring low levels of humidity.

It is another object of the present invention to provide a humidity-sensitive element which may be used for measuring humidity at high temperature conditions.

The aforementioned objects are achieved in accordance with the present invention by using a humidity-sensitive element comprising a high level of chromic oxide, i.e., 21 to 73 mol%, and further comprising 25 to 55 mol% of at least one member selected from the group consisting of ZnO and MgO, 0.5 to 8.0 mol% of CuO, 0.5 to 8.0 mol% of Li$_2$O and 0.5 to 8.0 mol% of V$_2$O$_5$. The humidity-sensitive element in accordance with the present invention has an electrical resistance range which is suitable for use over a wide range of humidity conditions, e.g., 500k$\Omega$ when the relative humidity is 30% and 10k$\Omega$ when the relative humidity is 90%, both resistance values being at an ambient temperature of 25° C. The humidity-sensitive element of the present invention also has a high degree of reliability, with little long-term variation even when it is kept at high temperatures for a long period of time.

The excellent properties of the humidity-sensitive element of the present invention are believed to be due to the fact that its structure is such that small amounts of CuO, Li$_2$O and V$_2$O$_5$ are present in the grain boundaries of the crystalline grains which consist essentially of Cr$_2$O$_3$ and ZnO (or ZnO and MgO or MgO alone).

The reason for carefully selecting the amount of Cr$_2$O$_3$ present in the element is that if the amount is less than 21 mol%, the resistance range of the humidity-sensitive element is very high, and if the amount of Cr$_2$O$_3$ exceeds 73 mol%, the long-term stability of the element is adversely effected at high temperature conditions.

The reason for carefully selecting the total amount of at least one member selected from the group consisting of ZnO and MgO is that if the amount is less than 25 mol%, the long-term stability of the element is also adversely effected at high temperature conditions, and if the amount exceeds 55 mol%, the resistance range of the element is unsuitably high. The adverse effects are the same whether ZnO or MgO are used or whether both are used together. The reason for carefully selecting the total amount of CuO is that if the amount is less than 0.5 mol%, stability of the element is again adversely effected at high temperature conditions, and if the amount exceeds 8.0 mol%, the sensitivity of the element at lower humidity levels decreases. The reason for carefully selecting the total amount of $Li_2O$ and $V_2O_5$ is that if the amount of each of these materials is less than 0.5 mol%, the resistance range of the element is unsuitably high, and if the amount of each material exceeds 8.0 mol%, stability of the element is adversely effected at high temperature conditions.

DETAILED DESCRIPTION OF THE PREFERRED EMBODIMENT

Figure 1:
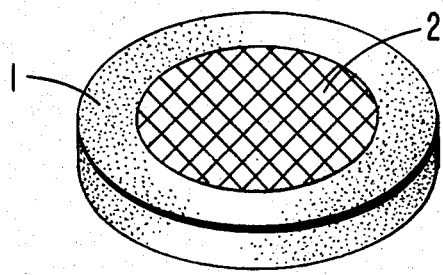
FIG. 1 is a perspective view of the humidity-sensitive element in accordance with the present invention.

Referring now to the drawings, the present invention will be explained in detail.

FIG. 1 shows a perspective view of the preferred embodiment of the invention in which the humidity-sensitive element comprises a humidity-sensitive body 1 and a pair of electrodes 2 attached to the respective surfaces of the body. Body 1 of the element is formed from sintered metal oxide and electrodes 2 are also formed from a metal oxide. A metal oxide electrode is desirable because of its stability, in particular, a ruthenium oxide electrode is more desirable because of its low cost. As shown in FIG. 1, lattice-shaped electrodes are utilized instead of plate-shaped electrodes known in the prior art. A humidity-sensitive element with lattice-shaped electrodes permits a substantial portion of the element body to be exposed to the environment. Thus, the element exhibits good sensitivity to changes in ambient humidity and has almost no hysteresis effect. Preferably, the electrodes are sufficiently porous to allow 30 to 50% of the total area of the body of the element under each of the electrodes to be exposed to the environment.

The humidity-sensitive element in accordance with the present invention is produced in the following manner. First, fine powders of chromic oxide ($Cr_2O_3$), zinc oxide ($Cr_2O_3$), cupric oxide (CuO), lithium carbonate ($Li_2CO_3$) and vanadium oxide ($V_2O_5$) are used as starting materials. The starting materials were weighed so as to give $Cr_2O_3$, ZnO, CuO, $Li_2O$, $V_2O_5$ mol ratios of 45%, 45%, 4%, 3% and 3%, respectively. The materials are then wet-mixed for 24 hours in a ball mill. After wet-mixing, the mixture is dried for 12 hours at 120° C. and then calcined at 800° C. The calcined material is pulverized for 24 hours in a ball mill and is dried again for 12 hours at 120° C. to form a powder. Next, 2 wt.% of polyvinyl alcohol is added to the powder as a binder. The mixture is then granulated in a granulating machine. The granulated material is then formed under 500 kg/cm² of pressure into a disc with a diameter of approximately 8 mm and a thickness of approximately 2 mm to form the body of the element. The disc is then sintered for 2 hours at a temperature of 1300° C. A ruthenium oxide paste is then screen-printed in a lattice-shaped configuration on each surface of the body to form the electrodes. The body is then heated to approximately 700° C. Thus a humidity-sensitive element is formed in accordance with the present invention.

Figure 2:
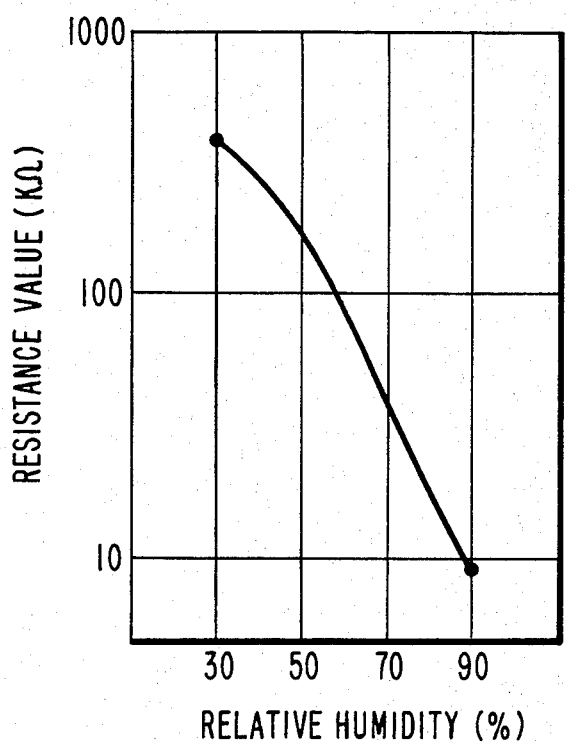
FIG. 2 is a graph showing the initial humidity-sensing characteristics of the humidity-sensitive element in accordance with one embodiment of the present invention.

FIG. 2 is a humidity characteristics curve for the above-described embodiment of the present invention. The curve was obtained under the condition that the relative humidity was varied over a range from 30% to 90% at a constant ambient temperature of 25° C. As can be seen from FIG. 2, the humidity-sensitive element of this invention exhibits relatively low resistance values over a wide range of humidity. As shown in FIG. 2, 420kΩ for 30% relative humidity and 9kΩ for 90% relative humidity at an ambient temperature of 25° C. Consequently, no matching network is required for connecting the element into an electrical circuit.

Figure 3:
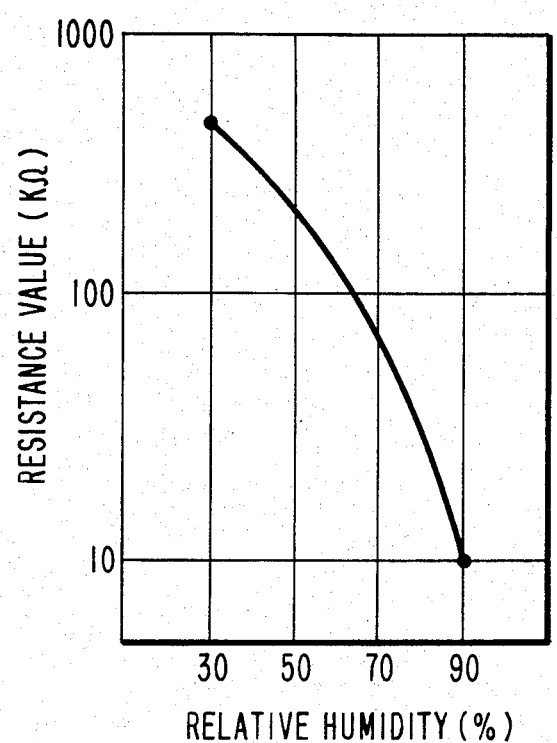
FIG. 3 is a graph showing the humidity-sensing characteristics of the humidity-sensing element of the embodiment in FIG. 2 after it has been maintained at a high temperature level.

FIG. 3 is a humidity characteristics curve obtained under the same conditions as described above; however, the humidity-sensitive element was maintained at a temperature of 85° C. for 1000 hours before the element was used to generate the curve. As can be seen from FIG. 3, the humidity characteristic of the element remains stable even after the element is exposed to a high temperature for an extended period of time.

Humidity-sensitive elements with the various compositions shown in Table 1 below were produced by the same process as explained above. The resistance of each of the elements of embodiments 2-7, as shown in Table 1, at relative humidities of 30% and 90% at an ambient temperature of 25° C. (initial humidity characteristics) were measured. The resistance of each embodiment was measured again under the same conditions after the element was maintained for 1000 hours at a temperature of 85° C. (humidity characteristics after storage at high temperature). The results are shown in Table 1. The humidity characteristics of the comparison examples 1-6, of which the compositions are outside the composition range specified for the present invention, are also shown in Table 1.

TABLE 1

| | Composition of Humidity Sensitive Body (mol %) | | | | | Initial Humidity Characteristic KΩ | | Humidity Characteristic After Being Kept in High Temperature | |
|---|---|---|---|---|---|---|---|---|---|
| | $Cr_2O_3$ | ZnO | CuO | $Li_2O$ | $V_2O_5$ | 30% RH | 90% RH | 30% RH | 90% RH |
| Embodiment # | | | | | | | | | |
| 2 | 42 | 42 | 8 | 4 | 4 | 275 | 12 | 280 | 15 |
| 3 | 45.5 | 46 | 0.5 | 4 | 4 | 420 | 7.5 | 560 | 8.0 |
| 4 | 40 | 40 | 4 | 8 | 8 | 270 | 5.3 | 320 | 5.2 |
| 5 | 48 | 48 | 3 | 0.5 | 0.5 | 820 | 26 | 900 | 32 |
| 6 | 35 | 55 | 4 | 3 | 3 | 690 | 33 | 740 | 41 |
| 7 | 65 | 25 | 4 | 3 | 3 | 530 | 19 | 620 | 24 |
| Comparison Example No. | | | | | | | | | |
| 1 | 43 | 43 | 10 | 2 | 2 | 160 | 27 | 165 | 31 |
| 2 | 45 | 44.8 | 0.2 | 5 | 5 | 490 | 5.0 | 720 | 7.5 |
| 3 | 39 | 39 | 2 | 10 | 10 | 340 | 4.9 | 630 | 6.5 |
| 4 | 46 | 47.6 | 6 | 0.2 | 0.2 | 1800 | 31 | 2300 | 45 |
| 5 | 15 | 70 | 5 | 5 | 5 | 2600 | 73 | 3200 | 89 |
| 6 | 81 | 10 | 3 | 3 | 3 | 970 | 44 | 1200 | 65 |

As understood from Table 1, humidity-sensitive elements in accordance with this invention represent a relatively low range of resistance values over a wide range of humidity and also have the property that they remain stable with the passage of time even under high temperature conditions. In contrast, the humidity-sensitive elements having a composition outside the composition range specified for the invention (namely, comparison examples 1–6) do not satisfy the above two conditions. That is, they do not have a low range of resistance values over a wide range of humidity and they do not remain stable over time under high temperature conditions.

In a further embodiment of the present invention, fine powders of chromic oxide, magnesium carbonate, cupric oxide, lithium carbonate and vanadium oxide are used as starting materials. These starting materials are measured so as to provide $Cr_2O_3$, MgO, CuO, $Li_2O$ and $V_2O_5$ mol ratios of 45%, 45%, 4%, 3%, 3%, respectively. In this embodiment, MgO is used rather than ZnO in the first embodiment described above. The materials are wet-mixed for 24 hours in a ball mill. After the mixture is dried for 12 hours at 120° C., it is calcined at 800° C. The calcined material is pulverized for 24 hours in a ball mill then dried again for 12 hours at 120° C. to provide a powder material. A humidity-sensitive element of the same construction as that shown in FIG. 1 is made by the same method as described above.

Figure 4:
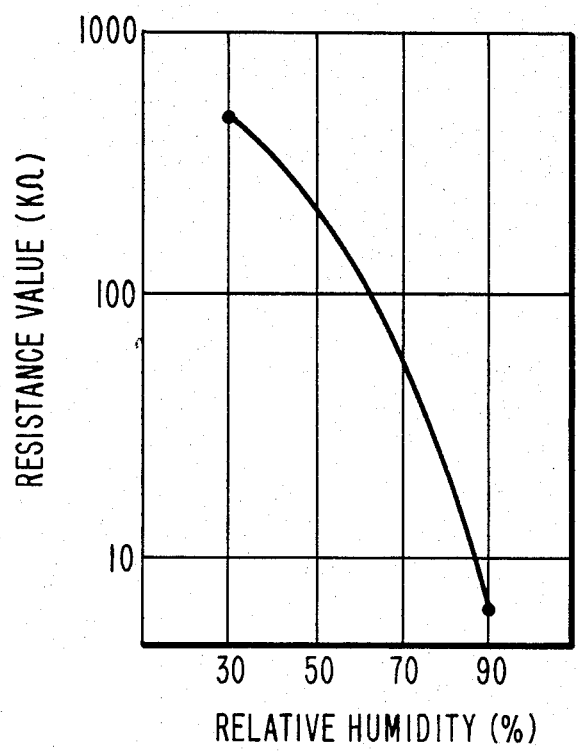
FIG. 4 is a graph showing the initial humidity-sensing characteristics of the humidity-sensing element in accordance with a further embodiment of the present invention.
Figure 5:
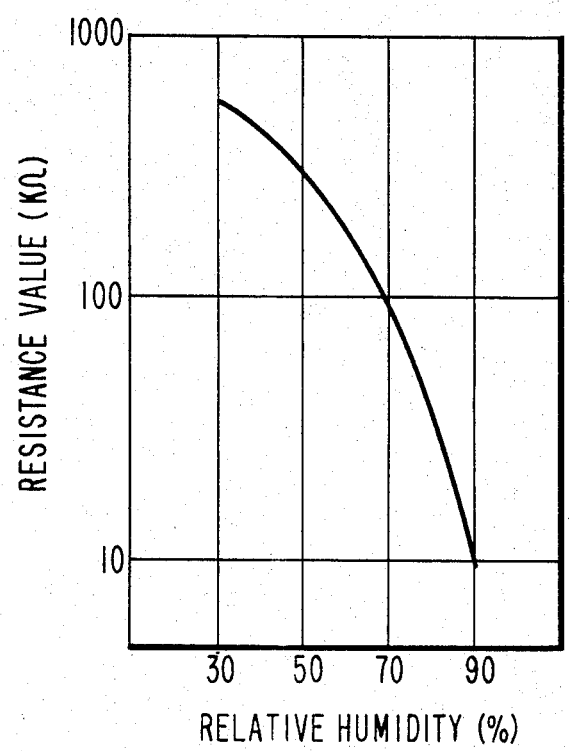
FIG. 5 is a graph showing the humidity-sensing characteristics of the humidity-sensing element of the embodiment in FIG. 4 after it has been maintained at a high temperature level.

A humidity characteristics curve for this embodiment of the invention is shown in FIG. 4 and is obtained under the conditions that the relative humidity is varied in the range of 30% to 90% at a constant ambient temperature of 25° C. As can be seen from FIG. 4, the humidity-sensitive element of the present embodiment also exhibits a low range of resistant values over a wide range of humidity. Namely, the resistant value at 30% and 90% relative humidity is 600kΩ and 7KΩ, respectively, at 25° C. of ambient temperature. The humidity characteristics curve shown in FIG. 5 is obtained under the same condition; however, the humidity-sensitive element was maintained at a temperature of 85° C. for 1000 hours prior to taking the measurements. As can be seen from FIG. 5, the humidity characteristic of the element remains stable after the element is exposed to a high temperature.

Humidity-sensitive elements with the composition shown in Table 2 below were produced by the same process explained above.

The resistance value of each elements of embodiments 9–14 as shown in Table 2, at relative humidities of 30% and 90% at ambient temperature of 25° C. (initial humidity characteristics) were measured. The resistance of each embodiment was measured again under the same conditions after the element was maintained for 1000 hours at a constant temperature of 85° C. (humidity characteristics after storage at high temperature). The results are shown in Table 2. The humidity characteristics of comparison examples 7 to 12, of which the compositions are outside the composition range specified for the present invention, are also shown in Table 2.

TABLE 2

| | Composition of Humidity Sensitive Body (mol %) | | | | | Initial Humidity Characteristic KΩ | | Humidity Characteristic After Being Kept in High Temperature | |
|---|---|---|---|---|---|---|---|---|---|
| | $Cr_2O_3$ | MgO | CuO | $Li_2O$ | $V_2O_5$ | 30% RH | 90% RH | 30% RH | 90% RH |
| Embodiment # | | | | | | | | | |
| 9 | 42 | 42 | 8 | 4 | 4 | 340 | 9.6 | 350 | 13 |
| 10 | 45.5 | 46 | 0.5 | 4 | 4 | 590 | 8.0 | 670 | 9.5 |
| 11 | 40 | 40 | 4 | 8 | 8 | 370 | 4.5 | 440 | 4.8 |
| 12 | 48 | 48 | 3 | 0.5 | 0.5 | 920 | 24 | 1100 | 37 |
| 13 | 35 | 35 | 4 | 3 | 3 | 860 | 49 | 1050 | 62 |

TABLE 2-continued

|  | Composition of Humidity Sensitive Body (mol %) | | | | | Initial Humidity Characteristic KΩ | | Humidity Characteristic After Being Kept in High Temperature | |
|---|---|---|---|---|---|---|---|---|---|
|  | $Cr_2O_3$ | MgO | CuO | $Li_2O$ | $V_2O_5$ | 30% RH | 90% RH | 30% RH | 90% RH |
| 14 | 65 | 25 | 4 | 3 | 3 | 820 | 13 | 1080 | 19 |
| Comparison Example No. | | | | | | | | | |
| 7 | 43 | 43 | 10 | 2 | 2 | 180 | 29 | 220 | 43 |
| 8 | 45 | 44.8 | 0.2 | 5 | 5 | 630 | 7.3 | 890 | 9.6 |
| 9 | 39 | 39 | 2 | 10 | 10 | 460 | 22 | 700 | 31 |
| 10 | 46 | 47.6 | 6 | 0.2 | 0.2 | 2000 | 150 | 2800 | 240 |
| 11 | 15 | 70 | 5 | 5 | 5 | 3600 | 270 | 4800 | 330 |
| 12 | 81 | 10 | 3 | 3 | 3 | 1600 | 110 | 3100 | 260 |

As understood from Table 2, humidity-sensitive elements in accordance with the present invention represent a low range of resistance values over a wide range of humidity and also have the property that they remain stable with the passage of time, even after high temperature conditions. In contrast, the humidity-sensitive elements having a composition outside the composition range specified for the invention (namely, comparison examples 7-12) do not satisfy the above two conditions. That is, they do not have a low range of resistance values over a wide range of humidity and they do not remain stable over time under high temperature conditions.

Humidity-sensitive elements with the composition shown in Table 3 below were produced by the same process explained above.

The resistance value of each elements of embodiments 15-20 as shown in Table 3, at relative humidities of 30% an 90% at an ambient temperature of 25° C. (initial humidity characteristic) were measured. The resistance value of each embodiment was measured again under the same conditions after the element was maintained 1000 hours at a constant temperature of 85° C. (humidity characteristic afer storage of high temperature). The humidity characteristics of comparison examples 13 and 14, of which the composition is outside the composition range specified for the present invention are also shown in Table 3.

of humidity and also have the property that they remain stable with the passage of time, even under high temperature conditions. In contrast, the humidity-sensitive elements having a composition outside the composition range specified for the invention (namely, comparison examples 13 and 14) do not satisfy the above two conditions. That is, they do not have a the low range of resistance values over a wide range of humidity and do not remain stable over time under high temperature conditions.

In order to analyze the structure of the humidity-sensitive element of the present invention, a quantitative analysis was performed as follows. By using starting materials comprising 40 mol% of $Cr_2O_3$, 45 mol% of ZnO, 4 mol% of MgO, 3 mol% of CuO, 4 mol% of $V_2O_5$, and 4 mol% of $Li_2O$, a humidity sensitive element was made by the same method as explained above. In order to analyze the composition of the glass layer surrounding the grains which have a spinel structure, the humidity-sensitive body was pulverized into a powder as is shown in the art. The powder was then poured into a solution of hydrochloric acid having a concentration of 6 normal and was kept there for 30 minutes in order to dissolve the glass layer. The grains having a spinel structure did not dissolved. When the solution containing the glass layer composition was analyzed, 6.8 mol% of ZnO, 1.9 mol% of MgO, 2.9 mol% of CuO, 4.0 mol% of $V_2O_5$, and 3.8 mol% of $Li_2O$ was

TABLE 3

|  | Composition of Humidity Sensitive Body (mol %) | | | | | | Initial Humidity Characteristic (KΩ) | | Humidity Characteristic After Being Kept in High Temperature | |
|---|---|---|---|---|---|---|---|---|---|---|
|  | $Cr_2O_3$ | ZnO | MgO | CuO | $Li_2O$ | $V_2O_3$ | 30% RH | 90% RH | 30% RH | 90% RH |
| Embodiment # | | | | | | | | | | |
| 15 | 45 | 43 | 2 | 4 | 3 | 3 | 430 | 7.5 | 455 | 9.5 |
| 16 | 45 | 40 | 5 | 4 | 3 | 3 | 520 | 9.0 | 550 | 11.0 |
| 17 | 45 | 5 | 40 | 4 | 3 | 3 | 600 | 9.0 | 640 | 11.5 |
| 18 | 35 | 50 | 5 | 4 | 3 | 3 | 740 | 41 | 930 | 53 |
| 19 | 65 | 20 | 5 | 4 | 3 | 3 | 690 | 17 | 870 | 22 |
| Comparison Example No. | | | | | | | | | | |
| 13 | 15 | 65 | 5 | 5 | 5 | 5 | 3100 | 140 | 3900 | 200 |
| 14 | 81 | 5 | 5 | 5 | 5 | 5 | 1100 | 82 | 2200 | 170 |

As can be seen from Table 3, humidity-sensitive elements in accordance with the present invention represent a low range of resistance values over a wide range measured, but the presence of $Cr_2O_3$ was not detected. From this analysis, it may be assumed that the humidity-sensitive element of the present invention comprises grains having a spinel structure comprising $ZnCr_2O_4$ and/or $MgCr_2O_4$, and a glass layer, i.e., an amorphous layer, comprising ZnO, MgO, CuO, $V_2O_5$ and $Li_2O$.

Although illustrative embodiments of the invention have been described in detail with reference to the accompanying drawings, it is to be understood that the invention is not limited to those precise embodiments and that various changes and modifications may be effected therein by one skilled in the art without departing from the scope or spirit of the invention.

We claim:

1. A humidity-sensitive element comprising:
   a humidity-sensitive body which consists essentially of about 21 to about 73 mol% $Cr_2O_3$, about 25 to about 55 mol% of at least one member selected from the group consisting of ZnO and MgO and mixtures thereof, about 0.5 to about 8.0 mol% of CuO, about 0.5 to about 8.0 mol% of $Li_2O$, and about 0.5 to about 8.0 mol% of $V_2O_5$; and
   a pair of electrodes attached to the body.

2. A humidity-sensitive element according to claim 1 wherein said electrodes are made of metal oxide.

3. A humidity-sensitive element according to claim 2 wherein said electrodes are made of ruthenium oxide.

4. A humidity-sensitive element according to claim 1 wherein said humidity-sensitive body comprises grains having a spinel structure including at least one member selected from the group consisting of $ZnCr_2O_4$ and $MgCr_2O_4$ and mixtures thereof, and a glass layer surrounding each of said grains which include CuO, $Li_2O$, $V_2O_5$ and at least one member selected from the group consisting of ZnO and MgO and mixtures thereof.

5. A humidity-sensitive element according to claim 1 wherein each of said electrodes are sufficiently porous that from 30 to 50% of a total area of the humidity-sensitive body under each of said electrodes is exposed.

6. A humidity-sensitive element according to claim 1 wherein each of said electrodes is a lattice-shaped electrode.

7. A humidity-sensitive element according to claim 5 wherein each of said electrodes is a lattice-shaped electrode.

8. A composition for use in forming a humidity-sensitive element, said composition consisting essentially of about 21 to about 73 mol% $Cr_2O_3$, about 25 to about 55 mol% of at least one member selected from the group consisting of ZnO and MgO and mixtures thereof, about 0.5 to about 8.0 mol% of CuO, about 0.5 to about 8.0 mol% of $Li_2O$, and about 0.5 to about 8.0 mol% of $V_2O_5$.

* * * * *